(12) United States Patent
Temple et al.

(10) Patent No.: US 8,960,496 B2
(45) Date of Patent: Feb. 24, 2015

(54) SLIDE PROCESSING APPARATUS AND METHOD

(75) Inventors: John Temple, Chester (GB); Ian Kerrod, Ewloe (GB); Alan Prile, Runcorn (GB); Roger Smith, Tyldesley (GB); Stephen Hankey, Wigan (GB)

(73) Assignee: Thermo Shandon Ltd (GB)

( * ) Notice: Subject to any disclaimer, the term of this patent is extended or adjusted under 35 U.S.C. 154(b) by 717 days.

(21) Appl. No.: 12/440,444

(22) PCT Filed: Sep. 8, 2007

(86) PCT No.: PCT/GB2007/003361
§ 371 (c)(1),
(2), (4) Date: Mar. 6, 2009

(87) PCT Pub. No.: WO2008/029144
PCT Pub. Date: Mar. 13, 2008

(65) Prior Publication Data
US 2010/0040439 A1 Feb. 18, 2010

(30) Foreign Application Priority Data
Sep. 8, 2006 (GB) .................................. 0617771.1

(51) Int. Cl.
*B65G 59/00* (2006.01)
*B65H 1/00* (2006.01)

(52) U.S. Cl.
USPC .............. 221/287; 221/208; 221/1; 221/18; 221/168; 221/180; 221/242; 221/241; 221/159; 221/172; 221/68; 221/264; 81/57.37; 81/433; 81/452; 81/190; 133/4 R; 133/1 R

(58) Field of Classification Search
CPC .................................. B65G 59/00; B65H 1/00
USPC ............... 221/287, 208, 1, 18, 168, 162, 180, 221/242, 241, 159, 172, 278, 68, 264; 81/57.37, 433, 452, 190; 133/4 R, 1 R
See application file for complete search history.

(56) References Cited

U.S. PATENT DOCUMENTS 1,637,549 A * 8/1927 Chandler ........................ 453/61
3,443,706 A * 5/1969 Puhm ............................ 414/801
(Continued)

FOREIGN PATENT DOCUMENTS

AU   2005203557 B1   8/2006
EP   0 798 550 A1   10/1997
(Continued)

OTHER PUBLICATIONS

International Search Report and Written Opinion mailed Feb. 29, 2008, from PCT Application No. PCT/GB2007/003361 (15 pages).
(Continued)

*Primary Examiner* — Rakesh Kumar
(74) *Attorney, Agent, or Firm* — Kilpatrick Townsend & Stockton LLP

(57) ABSTRACT

The present invention is concerned with a basket processing apparatus that includes a basket storage portion in a form of a horizontal load rail (2). A plurality of slide storage baskets (4) can be located in series on the rail (2). Each basket is "side loading" and the side loading aperture of each basket can be selectively covered by a slide retaining bar (6). When the baskets (4) are placed on the load rail (2) (e.g. by hooking or clipping the baskets onto the rail), the basket can be moved along the horizontal rail by a basket moving means. The arrangement of the rail and the basket moving means is such that the baskets can be pushed together and move as a "train". Baskets moved to the pick-up end (12) of the rail can then be removed from the rail and processed. A vertical lift mechanism can be used to remove the basket and transport it to a processing device, for example a coverslipper.

23 Claims, 12 Drawing Sheets

(56) References Cited

U.S. PATENT DOCUMENTS

| | | | |
|---|---|---|---|
| 3,833,449 A | | 9/1974 | Johnson |
| 3,847,301 A | * | 11/1974 | Shaw ............................. 221/5 |
| 3,972,423 A | | 8/1976 | Tipton |
| 4,033,809 A | | 7/1977 | Tipton |
| 4,176,670 A | * | 12/1979 | Repetti ........................ 453/18 |
| 4,488,662 A | * | 12/1984 | Fanning ...................... 221/197 |
| 5,209,903 A | | 5/1993 | Kanamori et al. |
| 5,588,555 A | * | 12/1996 | Kanamori et al. ............ 221/197 |
| 5,601,650 A | | 2/1997 | Goldbecker et al. |
| 5,690,892 A | * | 11/1997 | Babler et al. .................... 422/63 |
| 5,731,207 A | | 3/1998 | Seto |
| 5,812,692 A | | 9/1998 | Rosenlof et al. |
| 5,873,394 A | | 2/1999 | Meltzer |
| 5,989,386 A | | 11/1999 | Elliott |
| 6,076,583 A | | 6/2000 | Edwards |
| 6,436,348 B1 | * | 8/2002 | Ljungmann et al. ............. 422/63 |
| 6,568,447 B1 | | 5/2003 | Sakai et al. |
| 7,520,247 B2 | * | 4/2009 | Rutledge .................... 119/51.01 |
| 2003/0047567 A1 | | 3/2003 | Plank et al. |
| 2003/0090959 A1 | | 5/2003 | Mayer et al. |
| 2004/0092024 A1 | | 5/2004 | Reinhardt et al. |
| 2005/0186114 A1 | | 8/2005 | Reinhardt et al. |
| 2005/0230412 A1 | * | 10/2005 | Hakala ......................... 221/208 |
| 2005/0250211 A1 | | 11/2005 | Reinhardt et al. |
| 2005/0263082 A1 | * | 12/2005 | Rutledge .................... 119/51.01 |
| 2005/0282292 A1 | * | 12/2005 | Torre-Bueno ................. 436/180 |
| 2006/0005640 A1 | | 1/2006 | Osaka |
| 2006/0029266 A1 | | 2/2006 | Wetzel et al. |
| 2006/0077498 A1 | | 4/2006 | Izvoztchikov et al. |
| 2006/0105359 A1 | | 5/2006 | Favuzzi et al. |
| 2006/0148063 A1 | | 7/2006 | Fauzzi et al. |
| 2006/0266765 A1 | * | 11/2006 | Pugh ................................ 222/1 |
| 2008/0013089 A1 | | 1/2008 | Ishii et al. |
| 2008/0217354 A1 | * | 9/2008 | Newman et al. .............. 221/229 |
| 2008/0226126 A1 | | 9/2008 | Ohno |
| 2009/0139300 A1 | * | 6/2009 | Pugh et al. ..................... 73/1.36 |

FOREIGN PATENT DOCUMENTS

| | | |
|---|---|---|
| EP | 1 052 497 | 11/2000 |
| EP | 1 742 032 | 1/2007 |
| FR | 2374630 A1 | 7/1978 |
| GB | 1 466 561 | 3/1977 |
| GB | 2314451 A | 12/1997 |
| GB | 2 441 177 A | 2/2008 |
| JP | 070333123 | 12/1995 |
| WO | WO 94/14097 A1 | 6/1994 |
| WO | WO 99/20995 | 4/1999 |
| WO | WO 00/37986 A1 | 6/2000 |
| WO | WO 02/04123 A1 | 1/2002 |
| WO | WO 2004/059441 A2 | 7/2004 |
| WO | WO 2004/102163 A3 | 11/2004 |

OTHER PUBLICATIONS

International Preliminary Report on Patentability mailed Mar. 10, 2009, from PCT Application No. PCT/GB2007/003361 (11 pages).
Partial European Search Report from European Application No. 11160310.6 mailed Apr. 28, 2014 (7 pages).

* cited by examiner

SLIDE PROCESSING APPARATUS AND METHOD

This application is the U.S. National Phase entry under 35 U.S.C. §371 and claims the benefit of International Application No. PCT/GB2007/003361, filed Sep. 6, 2007, which claims the benefit of Great Britain Application No. 0617771.1 filed Sep. 8, 2006, the entire contents of which are hereby incorporated herein by reference.

The present invention is concerned with microscope slide processing apparatus and methods. In particular, the present invention relates to coverslipping apparatus as well as apparatus and methods for the handling of coverslips and slides.

The present invention has a number of aspects, which address different drawbacks that the present inventors have identified with existing slide handling and processing apparatus and methods. Some or all of the optional and preferred features of each of the aspects can apply to some or all of the other aspects.

As used herein, the term "slide" means a slide onto which a specimen, for example a pathology specimen can be mounted. Such slides are also known as microscope slides. Where reference is made to the sides or ends of a slide, this is intended as a reference to the longer sides or shorter sides of a rectangular slide respectively.

Furthermore, for ease of subsequent description the following definitions and explanations will use apparently absolute orientations such as "up", "down", "forward", "backward", "above" and "below" and analogous terms, for example with reference to the movement of a coverslip. However the descriptions concerned will apply equally to embodiments in other absolute orientations unless the context clearly requires otherwise.

Conventionally, when a plurality of slides is to be processed by a conventional coverslipper, stainer or other types of slide processing apparatus, they are placed in a slide storage basket. Typically such baskets hold several tens of slides. Known baskets are substantially rectangular in cross section to accommodate the rectangular slides. Known baskets typically support a slide along its sides and the slide is loaded and unloaded via an aperture in the basket corresponding to an end of the slide. Thus, conventional baskets provide an end loading arrangement.

Typically, a basket containing a plurality of slides is placed by a user in the slide processing apparatus and the basket and/or the individual slides are processed. The baskets are oriented so that the slides are vertical. For example, the basket of slides is introduced in its entirety into a staining solution or the slides are individually removed from the end of the basket, rotated, a coverslip applied to each one, and then rotated and returned to the basket. When all of the slides in the basket have been processed, the user removes the basket from the apparatus and replaces it with a new one.

In another example of a known slide processing apparatus, two baskets can be stored in the apparatus and processed sequentially. The baskets are located in a vertical storage chute and the processing apparatus removes baskets from the bottom of the chute. Again, slides are held vertically within the basket are removed from the end of the basket, rotated, coverslipped, rotated again and returned to the basket.

The present inventors have noted that not only are existing arrangements inefficient in terms of use of space, but they are also inefficient because of the requirement to rotate the slides.

The present invention addresses these drawbacks. At its most general, the present invention proposes that a slide processing apparatus is provided with a basket storage buffer that stores a plurality of baskets such that the baskets can be moved along the basket storage buffer in a direction that is substantially the same as the direction in which slides are loaded and unloaded from the basket. This means that less handling of the basket is required because the slides are easily accessible by the processing apparatus. It also represents an efficient use of space compared to known arrangements.

In an alternative or additional proposal, a basket processing apparatus is provided with a horizontal basket storage portion for storing a plurality of baskets. In a refinement of either or both of these proposals, the baskets are side loading baskets and the basket storage buffer stores the baskets so that the slides are horizontal.

In one aspect, the present invention provides a basket processing apparatus for use in a slide processing apparatus, said basket processing apparatus comprising a basket storage portion for storing a plurality of baskets, each basket being capable of storing a plurality of slides and having an aperture through which slides are unloaded in an unloading direction, and a basket moving means for moving the plurality of baskets along the basket storage portion in the unloading direction.

An advantage of this arrangement is that further manipulation of the baskets can be reduced or minimised. Preferably the baskets can be removed from an end of the basket storage portion and a slide unloaded from a basket by a slide retrieval mechanism without having to realign the basket or the slide.

Suitably in use the basket moving means moves the plurality of baskets simultaneously. Preferably the baskets are moved as a "train" along the basket storage portion.

Preferably the basket storage portion is horizontal and the basket moving means is adapted to move baskets horizontally along the basket storage portion.

In use, the baskets are preferably aligned on the basket storage portion so that the slides within the baskets are horizontal. In this way, the slides can be unloaded from a basket and coverslipped without having to rotate the slide.

Preferably the baskets are side loading baskets (i.e. slides can be loaded and unloaded via the side of the basket).

Suitably the basket storage portion comprises a rail to which baskets can be attached and moved along by the basket moving means.

Preferably the basket moving means includes a basket pusher that engages with the baskets to move them along the basket storage portion. Preferably the basket moving means includes a belt for driving the basket pusher.

Suitably the basket processing apparatus includes a lift mechanism for lifting a basket from the basket storage portion. Suitably the lift mechanism is for lifting the basket substantially vertically from the basket storage portion.

Suitably the basket processing apparatus includes two basket storage portions and one of the basket support portions is for storing processed baskets.

In a related aspect, the present invention provides a basket processing apparatus comprising a horizontal basket storage portion for storing a plurality of baskets.

In a related aspect, the present invention provides a slide processing apparatus that includes a basket processing apparatus according to the first aspect. Preferably the slide processing apparatus comprises a coverslipper.

In a related aspect, the present invention provides a basket for storing a plurality of slides, wherein the basket includes a connector portion for connecting the basket to a basket storage portion as defined above.

Suitably the basket storage portion includes a rail and the connector portion includes a rebate for receiving the rail. Preferably the connector portion provides a latched or snap-fit connection. Suitably the connector portion is adapted to receive the rail such that the basket is constrained to move along the rail. In this way the basket can only be removed from the rail or added to the rail by sliding it onto the end of the rail.

Preferably the connector portion is C-shaped, suitably with inturned end portions, so as to retain the basket on the rail and prevent the basket from being removed from the rail other than by sliding it along the rail.

Suitably the basket processing apparatus of the first aspect includes at least one, preferably more than one, basket as defined herein.

In a related aspect, the present invention provides a method of processing baskets in a basket processing system, wherein the method includes storing a plurality of baskets on a basket storage portion, the basket having an aperture through which slides are unloaded in an unloading direction, and moving the said plurality of baskets along the basket storage portion in the unloading direction.

Suitably, the basket remains attached to the basket storage portion as it is moved along. Preferably it is transferred to the next mechanism in the same direction of movement.

Preferably the method includes processing the baskets and storing a plurality of the processed baskets on a second basket storage portion.

In a related aspect, the present invention provides a method of processing baskets in a basket processing system, wherein the method includes storing a plurality of baskets on a horizontal basket storage portion. Suitably the baskets are stored on the basket storage portion so that the slides are horizontal. Preferably the baskets are moved horizontally along the basket storage portion.

As noted above, known baskets are end loading, i.e. slides are loaded and unloaded in a direction parallel to the sides of the slide. The present inventors have noted that this arrangement means that the slides are supported along their sides in the basket. This typically means that there is a significant contact area between the slide and the basket. This can cause the slide to "stick" to the basket, particularly after the slide has been coverslipped, in which case mountant or solvent may have spilled onto the basket.

At its most general, this aspect of the present invention proposes that a basket should be side loading rather than end loading. Also that the basket should be provided with means for selectively preventing slides from being loaded or unloaded during processing.

In a further aspect, the present invention provides a side loading basket for use in a coverslipper comprising an aperture through which slides can be loaded and unloaded, and a slide retaining member for selectively covering at least part of the aperture.

With this arrangement, the slides can be supported at their ends. In other words there is no need for support along the sides of the slide. This means that the contact area between the slide and the basket can be reduced, thereby preferably reducing the chance of the slide sticking to the basket.

In preferred embodiments a slide can be loaded into the basket through the aperture in a direction parallel to the ends of the slide.

In other words, it is preferred that the basket is adapted so that slides can be loaded sideways, i.e. the side of the slide (the longer side of a rectangular slide) is the leading edge of the slide as it is inserted into the basket.

Preferred embodiments also include the feature of the basket having a slide retaining member that can selectively cover at least part of the aperture. Preferably this is achieved by moving the slide retaining member in a direction parallel to the plane of the slides.

Preferably the slide retaining member is in a sliding arrangement with respect to the aperture. Preferably the sliding direction is parallel to the sides of the slide.

Suitably the basket includes guide means for engaging the slide retaining member, for example respective end portions of the slide retaining member. In preferred embodiments the guide means are associated with an upper portion of the basket, more preferably both upper and lower portions of the basket. The guide means can comprise a rail, preferably two rails, one on each of upper and lower portions of the basket. The guide means are preferably integral with the basket.

Alternatively or additionally, the slide retaining member is connected pivotally to the rest of the basket. For example, preferably the slide retaining member is hinged with respect to the rest of the basket.

Suitably the basket includes a fixed slide retaining structure located opposite the aperture. This preferably stops slides from falling out of that side of the basket.

Preferably the basket includes a support structure for supporting both ends of a slide. Preferably the support structure comprises ledges.

In a related aspect, the present invention provides a slide processing apparatus including a basket as defined above. Preferably the slide processing apparatus comprises a coverslipper.

In a related aspect, the present invention provides the use in a slide processing apparatus of a basket as defined above. Preferably the slide processing apparatus comprises a coverslipper.

As is known, coverslipping equipment consists of a considerable number of moving mechanisms that manipulate coverslips and microscope slides. For adequate operator safety it is necessary to enclose the moving parts behind guards or covers.

Furthermore, the slides are typically kept under liquids (for example Xylene) to prevent the specimen on the slide from drying out. Operators typically wear gloves for protection against the effects of the chemicals used and this can hinder the easy use of some types of controls such as buttons and switches. The use of touchscreens is undesirable as the chemicals can leave residue marks across the screen and the touch position accuracy is degraded by the wearing of gloves.

In addressing this problem, the present invention proposes that the safety guard or cover is integrated with a start or activation switch so that coverslipping can be initiated when the guard or cover is closed.

In a further aspect, the present invention provides a slide processing apparatus having a slide processing mechanism and a cover, the cover being moveable between an open position which provides access to the slide processing mechanism and a closed position which does not provide access to the slide processing mechanism, wherein the slide processing mechanism is activated by moving the cover into the closed position.

This arrangement means that the user does not have to depress any switches or manipulate any controls in order to start processing of the slides.

Suitably the slide processing apparatus includes cover control means for detecting the cover when it is in the closed position and activating the slide processing mechanism.

Preferably the cover control means includes a detector for detecting whether a basket is associated with the slide processing mechanism and, if a basket is detected, the cover control means activates the slide processing mechanism. Suitably the slide processing mechanism includes a basket storage portion as defined above and the cover control means detects whether a basket is located on the basket storage portion.

Preferably the slide processing apparatus comprises a coverslipper.

In a related aspect, the present invention provides a method of operating a slide processing apparatus comprising a slide processing mechanism and a cover that is moveable between an open position which provides access to the slide processing mechanism and a closed position which does not provide access to the slide processing mechanism, wherein the method includes activating the slide processing mechanism by moving the cover into the closed position.

Preferably the method includes the step of detecting whether a basket is associated with the slide processing mechanism and, if a basket is detected, activating the slide processing mechanism.

In a further proposal, at its most general, the present invention proposes that a guard or cover should be held in a closed position whilst a slide processing mechanism is in operation. This use of an interlock whose operation is linked to the status of the slide processing mechanism preferably improves operator safety.

In a further aspect, the present invention provides a slide processing apparatus comprising a slide processing mechanism and a cover, the cover being moveable between an open position which provides access to the slide processing mechanism and a closed position which does not provide access to the slide processing mechanism, wherein the slide processing apparatus includes a locking means that is activated by operation of the slide processing mechanism to prevent the cover being moved from a closed position during operation of the slide processing mechanism.

Preferably the slide processing apparatus includes locking control means for detecting whether the slide processing mechanism is in operation. Suitably the slide processing mechanism comprises a coverslipper.

In a related aspect, the present invention provides a method of operating a slide processing apparatus comprising a slide processing mechanism and a cover, the cover being moveable between an open position which provides access to the slide processing mechanism and a closed position which does not provide access to the slide processing mechanism, the method including detecting operation of the slide processing mechanism and retaining the cover in a closed position during operation of the slide processing mechanism.

A further drawback identified by the present inventors is that a given basket is compatible only with a single type of basket processing apparatus or slide processing apparatus. For example, slides are loaded into a basket that is compatible with a particular stainer, the slides are stained but the slides then need to be transferred to a second basket so that they can be processed by a coverslipper. This is because the stainer and coverslipper have incompatible basket connections.

In addressing these problems, the present invention proposes that a basket should be provided with two different connectors so that it can be compatible with two basket or slide processing apparatuses.

In a further aspect, the present invention provides a basket for storing a plurality of slides, the basket having a first connecting means for connecting the basket to a basket processing apparatus, and a second connecting means for connecting the basket to a basket transfer mechanism of a slide processing apparatus such that the basket can be processed by the basket processing apparatus and by the slide processing apparatus.

Preferably the first connecting means includes a frame member that defines an aperture for receiving a basket engaging member associated with the basket processing apparatus.

Suitably the frame member is continuous and the aperture is enclosed by the frame member. Preferably this arrangement forms an "eye" connector (the basket engaging member being insertable through the "eye" so that the basket can be held or mounted on the basket engaging member).

Alternatively the frame member is not continuous and the aperture is partially enclosed by the frame member. Preferably the frame member comprises a pair of arms with opposing inturned portions.

Preferably the first connecting means comprises a hook portion. Preferably the hook portion includes a notched member, which notch is for cooperating with a basket engaging member associated with the basket processing apparatus.

Preferably the second connecting means comprises a connector portion as defined above for engagement with a basket storage portion.

Suitably the basket processing apparatus comprises a stainer. Suitably the slide processing apparatus comprises a coverslipper.

In a related aspect, the present invention provides a set of baskets, each of the baskets being as defined above, wherein at least two baskets have different first connecting means and the second connecting means of each of the baskets is the same.

In a related aspect, the present invention provides a basket processing apparatus including a basket as defined above. Preferably the basket processing apparatus comprises a stainer.

In a related aspect, the present invention provides a slide processing apparatus including a basket as defined above. Preferably the slide processing apparatus comprises a coverslipper.

In a related aspect, the present invention provides the use of a basket as defined above in a basket processing apparatus. Preferably the basket processing apparatus comprises a stainer.

In a related aspect, the present invention provides the use of a basket as defined above in a slide processing apparatus. Preferably the slide processing apparatus comprises a coverslipper.

In a related aspect, the present invention provides a method of processing a basket, the method including connecting the basket to a basket processing apparatus, processing the basket, connecting the basket to a slide processing apparatus and processing the slides.

Typically the basket will be connected to the slide processing apparatus manually, i.e. a user will move the basket from the basket processing apparatus (e.g. stainer) to the slide processing apparatus (e.g. coverslipper). Suitably the basket is as defined above.

The present inventors have noted that in order to coverslip slides in a given basket it is necessary to remove each slide in turn, apply the coverslip and return the slide back in to the basket. Removing slides quickly and accurately from the basket one at a time requires knowledge of a) if there is a slide there and b) its exact location in respect to the gripping device which pulls out the slide. This can be a challenging requirement and errors in alignment of the slide or gripping device can cause damage to a slide and even loss of samples.

At its most general, the present invention proposes that image of the slide and/or gripping device can be obtained and that image processed to identify a property of the slide, for example the position of the slide. Thus, using images from e.g. a camera, the detection of basket type can be automated, making for quicker processing.

By using an image from an image generating means (e.g. a camera) to detect gripper/slide features, rapid calculation of position information can be achieved as well as a reduction in stoppages and down time due to missing, damaged or misaligned slides.

In a further aspect, the present invention provides a slide detector for detecting at least one property of a slide, the slide detector comprising an image generating means for generating an image of the slide, and image processing means for identifying the at least one property of the slide based on the generated image.

Preferably the slide detector is for use in a slide processing apparatus. Suitably the slide processing apparatus comprises a coverslipper.

Preferably the at least one property of the slide comprises the position of the slide with respect to a slide processing mechanism.

Preferably the image processing means is configured to identify at least one edge of the slide. Suitably the image processing means is configured to make a plurality of measurements from the generated image so as to identify the edge.

Preferably the slide processing mechanism includes a slide gripper and the slide detector detects the position of the slide with respect to slide gripper.

Preferably the image generating means is configured to generate an image of the slide gripper. Preferably the image processing means is configured to identify at least one edge of the slide gripper.

Preferably the image generating means comprises a camera. Alternatively or additionally the image generating means comprises a linear sensor array. Alternatively or additionally, the image generating means comprises a charge coupled device.

Preferably the image generating means can detect one or both of light intensity and colour.

Preferably the image processing means includes a processor. Preferably the image processing means includes software. Conventional image processing techniques and algorithms can be used.

Preferably the image processing means is configured to identify the alignment of a slide with respect to a basket in which the slide is located. Preferably the image processing means is adapted to identify whether the slide has a predetermined alignment.

Preferably the slide detector is configured to identify whether a slide is present in a slot of a basket in which the slide is located. Suitably the image generating means is configured to generate an image of at least one of the slots of the basket and the image processing means is configured to measure the colour or intensity gradient of the part of the image corresponding to the slot.

Preferably the image processing means is configured to identify the thickness of a slide.

Preferably the slide detector is configured to generate a plurality of images of the slide so that the at least one property of the slide can be detected as a function of time.

Preferably the slide detector is associated with a slide processing apparatus comprising a slide processing mechanism, and the slide processing mechanism is moveable with respect to the slide in response to the detected at least one property of the slide.

Preferably the at least one property of the slide is the position of the slide with respect to the slide processing mechanism.

In a related aspect, the present invention provides a slide processing apparatus including a slide detector as defined above. Suitably the slide processing apparatus comprises a coverslipper.

In a related aspect, the present invention provides a method of detecting at least one property of a slide, the method including generating an image of the slide and processing the image to detect the at least one property.

Preferably the at least one property is the position of the slide with respect to a slide processing mechanism.

Preferably the method includes the step of moving the slide with respect to the slide processing mechanism in response to the detected slide position.

Preferably the detection of the slide position is repeated during movement of the slide. Suitably the detected slide position is then used to direct subsequent movement of the slide and/or slide processing mechanism.

Preferably the step of generating an image includes detecting one or both of light intensity and colour.

Preferably the method includes the step of averaging a plurality of values from the generated image.

In a related aspect, the present invention provides the use of an image generating means and an image processing means to detect at least one property of a slide.

Preferably the slide is located within a slide processing apparatus. Suitably the slide processing apparatus comprises a coverslipper.

The present inventors have noted that the advantages of using an image generating means and an image processor to identify properties of a slide such as the position of the slide also apply to the identification of properties associated with a basket.

Accordingly, in a further aspect, the present invention provides a basket detecting device for detecting at least one property of a basket for storing slides in a slide processing apparatus, the basket detecting device comprising an image generating means for generating an image of at least part of the basket, and image processing means for identifying the at least one property of the basket based on the generated image.

The preferred features relating to the image generating means and the image processing means described above in relation to the slide detecting device can also apply to the basket detecting device.

Preferably the image processing means is configured to identify a structural feature of the basket. Suitably the structural feature of the basket comprises a slide retaining member as defined above.

Suitably the image processing means identifies the colour of the structural feature. Alternatively or additionally, the image processing means identifies the shape of the structural feature. Alternatively or additionally the image processing means identifies the size of the structural feature.

Preferably the basket detecting device includes a basket property look-up means for retrieving predetermined basket property information in response to the detected at least one property. For example, the basket property information includes basket processing information. Thus, a user can provide a processing protocol that is associated with a particular basket or basket type.

In a related aspect the present invention provides a method of detecting at least one property of a basket for storing slides in a slide processing apparatus, the method including generating an image of at least part of the basket and processing the image to identify the at least one property of the basket based on the generated image.

Suitably the at least one property includes the type of basket.

Preferably the method includes processing the basket based on the detected at least one property.

In a related aspect, the present invention provides the use in a slide processing apparatus of a basket detecting device as defined above. Preferably the slide processing apparatus comprises a coverslipper.

In a related aspect the present invention provides a basket having a signal means that is detectable by a basket detecting device as defined above.

Alternatively or additionally, the signal means comprises a contrast member associated with the basket, which contrast member has either or both of the properties of (i) a colour that is different from the colour of the rest of the basket, and (ii) substantially linear edges delineating the contrast member from the rest of the basket.

Preferably the contrast member comprises the slide retaining member as defined above.

In a related aspect, the present invention provides a set of baskets, wherein at least two of the baskets have different signal means.

The present inventors have noted that known slide transport devices for unloading slides from a basket work by gripping opposite sides of the slide and then pulling the slide out from the end of the basket, i.e. end unloading. This requires two motors—one to bring the gripper to bear on the side of the slide, and another to move the gripper in the unloading direction. This makes the apparatus complex and bulky.

The present invention addresses this drawback and at its most general it proposes that the slide transport device should remove the slide from the side of the basket.

In a further aspect, the present invention provides a slide transport device for transporting a slide from a basket in a slide processing apparatus, the slide transport device including two slide engaging portions for engaging respective opposite sides of the slide, wherein the slide transfer device is adapted so that the slide is removed from the basket along a slide removal axis, which slide removal axis is perpendicular to the said opposite sides of the slide.

Preferably the slide engaging portions are constrained to move along a common axis, which common axis is the slide removal axis.

Preferably the separation between the two slide engaging portions is variable.

Preferably only one of the slide engaging portions is driven by a motor. Preferably the motor is a stepper motor. Suitably the motor controls the separation between the slide engaging portions and also the displacement of the slide engaging portions along the slide removal axis.

Preferably the slide engaging portions are connected via a linkage. Preferably the linkage includes biasing means to bias the slide engaging portions towards each other.

Preferably the slide transport device includes a stop member that cooperates with the linkage to cause (i) both slide engaging portions to move apart when one of the slide engaging portions is moved away from the other slide engaging portion, and (ii) both slide engaging portions to move together when the said one of the slide engaging portions is moved towards the said other slide engaging portion.

In a related aspect, the present invention provides a slide processing apparatus including a slide transport device as defined above. Suitably the slide processing apparatus comprises a coverslipper.

In a related aspect, the present invention provides a method of transporting a slide from a basket in a slide processing apparatus, wherein the method includes holding the slide at respective opposite sides of the slide and removing the slide from the basket along a slide removal axis that is perpendicular to the said opposite sides of the slide.

Preferably the method includes applying a coverslip to the slide. Suitably the method includes returning the slide to the basket.

In a related aspect, the present invention provides the use in a slide processing apparatus of a slide transport device as defined above. Suitably the slide processing apparatus comprises a coverslipper.

The present inventors have also noted that the width of a glass slide can vary and as it is desirable to place the coverslip in the middle, it can be important to know the width of the slide. In conventional coverslippers, slide width detection is difficult or impossible.

The present invention addresses this difficulty and at its broadest proposes that the separation of two slide engaging portions of a slide gripper can be measured and the width of the slide calculated based on that measurement.

In a further aspect, the present invention provides a slide transport device for use in a slide processing apparatus, the slide transport device including slide width measuring means.

Preferably the slide transport device includes slide engaging portions for holding the slide, and a sensor for detecting the separation between slide engaging portions when the slide is held between said slide engaging portions. Preferably the slide engaging portions are associated with signal means that are detectable by the sensor. Suitably the sensor is an optical sensor.

Preferably the slide transport device is adapted to move a slide from a first position to a second position wherein the slide transport device includes slide movement measuring means for measuring the distance travelled by the slide. Preferably the slide movement measuring means comprises a stepper motor. Preferably the slide movement measuring means is adapted to process a signal received from the stepper motor, which signal provides information relating to the distance moved by the slide.

In a related aspect, the present invention provides a slide processing apparatus including a slide transport device as defined above.

In a related aspect, the present invention provides a method of measuring the width of a slide in a slide processing apparatus, which slide processing apparatus includes a slide transport device comprising slide engaging portions for moving the slide, the method including measuring the separation between the slide engaging portions.

Preferably the slide processing apparatus comprises a coverslipper.

In a related aspect, the present invention provides the use in a slide processing apparatus of a slide transport device as defined above. Preferably the slide processing apparatus comprises a coverslipper.

The present inventors have also noted the slide thickness can vary and the glass coverslip needs to be placed accurately on the top face to aid the coverslip assembly process. Thus, in conventional coverslippers, slides can be damaged as a result of misjudging the location of the top face of the slide.

The present invention addresses this drawback and at its broadest it proposes that the top face of the slide can be calculated by holding the slide in a slide holding device so that the slide is a fixed distance from a reference surface whose location can be measured.

In a further aspect, the present invention provides a slide holding device comprising at least one slide engaging portion, which slide engaging portion is for engaging the edge of a slide, wherein the slide engaging portion includes a notch for receiving the edge of a slide, wherein a first notch face lies in a plane parallel to the upper surface of the slide and a second notch face forms an acute angle with the first notch face.

Preferably the said one of the faces of the notch lies in a horizontal plane. Preferably the notch is tapered.

In a related aspect, the present invention provides a slide engaging portion as defined above.

In a related aspect, the present invention provides a method of identifying the position of at least one of the faces of a slide, which method includes holding the slide in a slide holding device as defined above and identifying the position of the first notch face.

In a related aspect, the present invention provides the use in slide processing apparatus of a slide holding device as defined above. Preferably the slide processing apparatus comprises a coverslipper.

The reliability of pathology laboratory equipment is critical due to the important nature of the specimens processed in them. They cannot sometimes be duplicated if destroyed/damaged. It can sometimes be the case that the instruments can identify a fault has occurred (particularly with sophisticated modern control systems) and it then needs to either issue an audible/visible alarm to the user to retrieve the specimens or else it needs to protect the specimens in some way until an operator identifies the problem.

However, the present inventors have noted that known slide processing devices do not alert a user when something has gone wrong or if consumable need replenishing.

The present invention addresses this drawback and at its broadest proposes that a remote communication system is used to alert an operator. This means that an operator can leave the instrument unattended but still be alerted in the event of a problem.

In a further aspect, the present invention provides a sample processing apparatus including a sample processing system, a monitoring system for monitoring the processing of a sample and/or the status of the sample processing system, and a communications system for alerting a user as to the status of the processing of the sample and/or the status of the sample processing system, wherein the communications system includes a remote communications device for sending status information to a remote location.

Preferably the remote communications device comprises a modem. Preferably the modem is part of a network.

It is possible for instruments to communicate via network systems, wireless or otherwise, to provide data to laboratory management systems, other laboratory instruments or other devices or systems that may benefit from the information.

Suitably a central control system could advise which instruments need attention for consumable replenishment.

For example the instrument could use a modem to send a text or voice message to a mobile phone, pager or similar device kept by the operator Alternatively or additionally, the remote communications device comprises a radio signal transmitter. Preferably the remote communications device comprises an SMS transmitter. Preferably the remote communications device comprises a voice message transmitter.

Suitably the status information comprises information relating to the progress of the processing of one or more samples. Preferably the status information comprises information relating to the location of a particular sample. For example an operator may wish to know where a particular patient slide is in the system. The control system could communicate with the laboratory equipment, determine where it is, and even report when the slide will have completed the full process through the laboratory based on the current workload.

Preferably the communications system generates an alarm that is transmitted to a user in the event of a predetermined condition being detected by the monitoring system. Suitably the predetermined condition comprises insufficient consumables.

Preferably the sample processing apparatus comprises a coverslipper.

In a related aspect, the present invention provides a method of operating a slide processing apparatus, which method comprises monitoring the processing of the sample and of the status of the apparatus, and sending status information to a remote location.

Preferably the sample processing apparatus comprises a coverslipper.

In current auto-coverslipping machines the glass coverslips are loaded in to machine directly by hand. This has two main problems. Firstly, the operator is put at risk due to the potential of cutting themselves on the sharp glass. Secondly, contaminants on the operator's hands can be passed onto the coverslips which can affect the quality of the finished sample. Plus moisture from the operators hands can cause the coverslips to stick together causing jams within the machine.

There is therefore a the health and safety issue associated with handling of glass, plus also the risk of contaminating the coverslips with moisture, grease and other contaminates from the operators fingers.

The present invention addresses these drawbacks and at its most general proposes that a container for holding the coverslips should protect the coverslips from the environment during storage and transit, but which also forms part of the coverslip hopper within the coverslipper. The user can therefore load coverslips into the container (hopper) and then transfer the container to the coverslipper where the coverslips can be dispensed directly from the container. This removes the need for the operator to handle the coverslips directly when loading the coverslipper with new coverslips. The proposal of this design is to have a hopper to hold a stack of coverslips to offer protection during storage and transit but can also be loaded directly into an auto-coverslipping machine without the need for the operator to handle the glass directly.

In a further aspect, the present invention provides a hopper for storing a plurality of coverslips prior to dispensing of said coverslips by a coverslip dispensing device, wherein the hopper includes locating means for cooperating with the coverslip dispensing device so as to align the hopper with respect to the coverslip dispensing device.

Preferably the locating means are adapted so that aligning the hopper with the coverslip dispensing device causes coverslips inside the hopper to be aligned within the hopper.

Preferably the locating means comprise at least one recess for receiving an upstanding member located on the coverslip dispensing device. Suitably the at least one recess is tapered.

In preferred embodiments, preferably the at least one recess comprises at least one recess for receiving elongate members upstanding from the coverslip dispensing device.

Preferably the at least one recess is or are formed so that when the hopper is located on the coverslip dispensing device, the upstanding member of the coverslip dispensing device extends at least partially into the hopper.

Suitably the hopper has front and back walls, and a pair of opposing sidewalls, and the locating means are formed in the sidewalls.

Preferably the hopper is made from a plastics material. Preferably the hopper is made from a one-piece moulding. Suitably the hopper is disposable.

In an alternative or additional development of the idea of a hopper that can be loaded externally to the coverslipper and then located on the coverslipper for processing, the present invention provides a hopper for storing a plurality of coverslips prior to dispensing of said coverslips by a coverslip dispensing device, wherein said hopper includes an opening means that selectively provides an opening through which coverslips can be loaded into the hopper.

Preferably the hopper includes front and rear end walls and a pair of sidewalls, wherein said opening means comprises at least one of the hopper walls that is moveable with respect to the other walls so as to selectively provide an opening through which coverslips can be loaded into the hopper.

Suitably the at least one hopper wall is hinged with respect to the other walls so as to provide a hinged opening for loading the hopper.

Preferably the hopper includes a latch so that the at least one hopper wall can be selectively held in a closed position.

Preferably the hopper is made from a plastics material. Preferably the hopper is made from a one-piece moulding. Suitably the hopper is disposable.

In an alternative or additional development of the idea of a hopper that can be loaded externally to the coverslipper and then located on the coverslipper for processing, the present invention provides a hopper for storing a plurality of coverslips prior to dispensing of said coverslips by a coverslip dispensing device, wherein said hopper includes internal guide means for locating coverslips within the hopper.

Preferably the hopper includes a plurality of walls defining the internal volume of the hopper, and the internal guide means define a space within the hopper that is smaller than the internal volume of the hopper. This allows a coverslip smaller than the hopper to be stored in the hopper. It also means that the same external dimensions of the hopper can be maintained, whilst the position of the internal guide means can be formed so as to accommodate different coverslip sizes.

Preferably the internal guide means are arranged to reduce the effective length of the hopper.

Typically the internal guide means comprises one or more ribs. Preferably the ribs extend substantially from the bottom of the hopper to the top of the hopper.

Preferably the hopper is made from a plastics material. Preferably the hopper is made from a one-piece moulding. Suitably the hopper is disposable.

The present invention also proposes that a coverslipper should be provided with locating means for cooperating with a corresponding feature on a hopper so as to align the hopper with respect to the coverslipper.

In a further aspect, the present invention provides a coverslip dispensing device comprising hopper aligning means for cooperating with locating means on a hopper.

Suitably the hopper is as defined above.

Preferably the hopper aligning means comprise a locating pin, preferably a plurality of locating pins. Suitably two locating pins are provided side by side. Preferably they are arranged so as to cooperate with locating means on the sidewall of a hopper.

Preferably the locating pins are tapered.

In a further development, the present invention proposes that a carriage mechanism for a coverslipper should be provided with a tapered portion for moving under a stack of coverslips, and a coverslip receiving portion separated from the tapered portion by a step, such that a coverslip can be received onto the coverslip receiving portion and dispensed from the stack by engaging with the step.

In a further aspect the present invention provides a coverslip dispensing device comprising a dispensing carriage moveable between a retracted position and an extended position, wherein the dispensing carriage has a tapered portion and a coverslip receiving portion for supporting a coverslip, the respective portions being separated by a step extending transversely across the carriage.

Preferably the coverslip receiving portion is planar. Suitably it extends across the full width of the carriage.

Preferably the front portion of the carriage is wedge-shaped.

Whilst aspects of the present invention have been defined primarily in terms of an apparatus, it is to be understood that the features relating to the apparatus can also apply to the methods and uses described herein.

Each of the aspects previously described may be combined with one, more than one or all of the other aspects and features within each of the aspects may be combined with features from the other aspects. Therefore, in a further aspect, the present invention provides a combination of one, more than one or all of the previous aspects.

Embodiments of the invention are described below, by way of example only, with respect to the accompanying drawings, in which.

Figure 1:
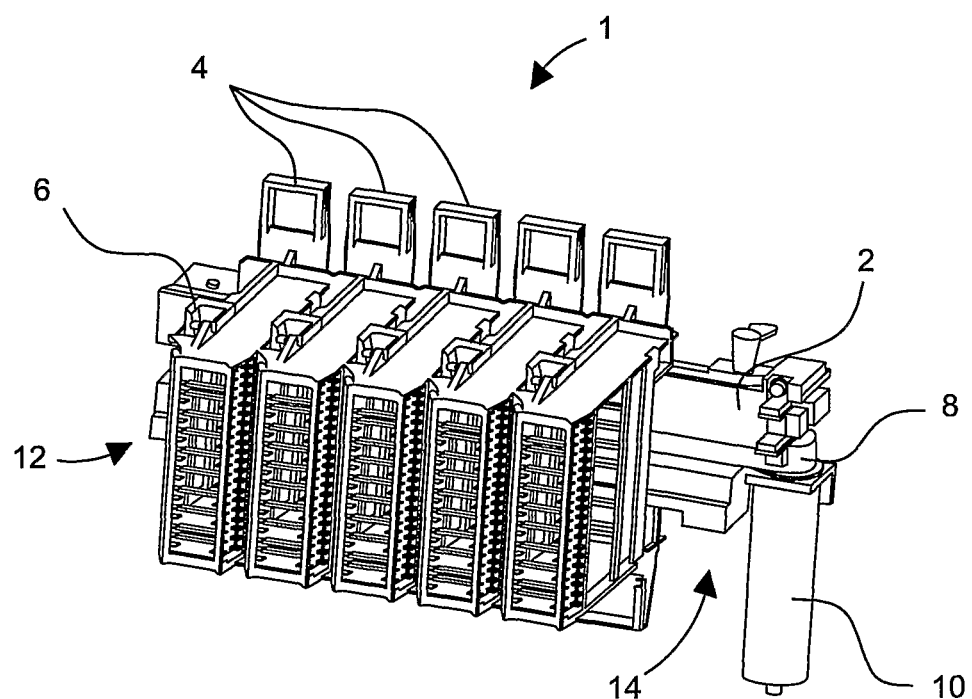
FIG. 1 shows a horizontal basket load rail, being an embodiment of the present invention.

FIG. 1 shows a basket storage device 1 that includes a basket storage portion in the form of a horizontal load rail 2. A plurality of slide storage baskets 4 are located in series on the rail 2. The basket storage device in this embodiment is located in a coverslipper (not shown).

Each basket is "side loading" as discussed with respect to other aspects of the invention. In FIG. 1, the side loading aperture of each basket is partially covered by a slide retaining bar 6. This arrangement is discussed in more detail with respect to FIG. 2.

Each basket 4 is attached to the horizontal load rail 2 by a connector (not shown). The connector is discussed in more detail below with respect to FIGS. 3 to 8.

When the baskets 4 are placed on the load rail 2 by a user (e.g. by hooking or clipping the baskets onto the rail), and the basket storage device is activated (e.g. by closing the cover or door of the coverslipper) the baskets are moved by a basket pusher (not shown) that is driven by a belt 8 that is in turn powered by a motor 10. The baskets are moved towards the basket pick-up end 12 of the rail. If there is more than one basket on the rail, this movement will cause the baskets to be pushed together and move as a "train".

The basket located at the pick-up end 12 can then be removed from the rail and processed. For example, a vertical lift mechanism can be used to remove the basket from the rail and transport it to a processing device, for example a coverslipper.

Thus, the baskets are moved along the rail in the same direction as the individual slides are unloaded from the baskets. Baskets removed from the basket pick-up end 12 of the rail are therefore already aligned so that the "side loading" aperture of the basket is easily accessible.

A user can attach additional baskets to the rail by adding them to the loading end 14 of the rail 2. Indeed, this arrangement allows one or more baskets to be loaded at the same time.

In other embodiments, the basket storage portion is used to store baskets that have been processed, i.e. an output basket storage buffer. In such embodiments, the output buffer can be used to safely store processed baskets until they are removed by the operator. This allows baskets to be removed in any sequence. Indeed, priority baskets which have been processed can be unloaded leaving others on the output rail.

The use of a horizontal load and unload rail can optimise the use of space. In preferred embodiments, two basket storage portions are provided, for example an input rail for baskets waiting for processing and an output rail for processed baskets.

An advantage of storing side loading baskets on a horizontal rail is that the basket is offered to the basket processing part of a coverslipper so that the slide is presented horizontally. This means that there is no need for further reorientation before a coverslip is applied.

Suitably, the baskets are adapted so loading in the wrong orientation is not possible. In this embodiment, the connector on the basket may only permit the basket to be connected to the rail in one orientation.

The benefits demonstrated by this embodiment include optimised buffer capacity for the available space. A further advantage is that the slides are presented in the correct orientation for coverslipping.

Figure 2:
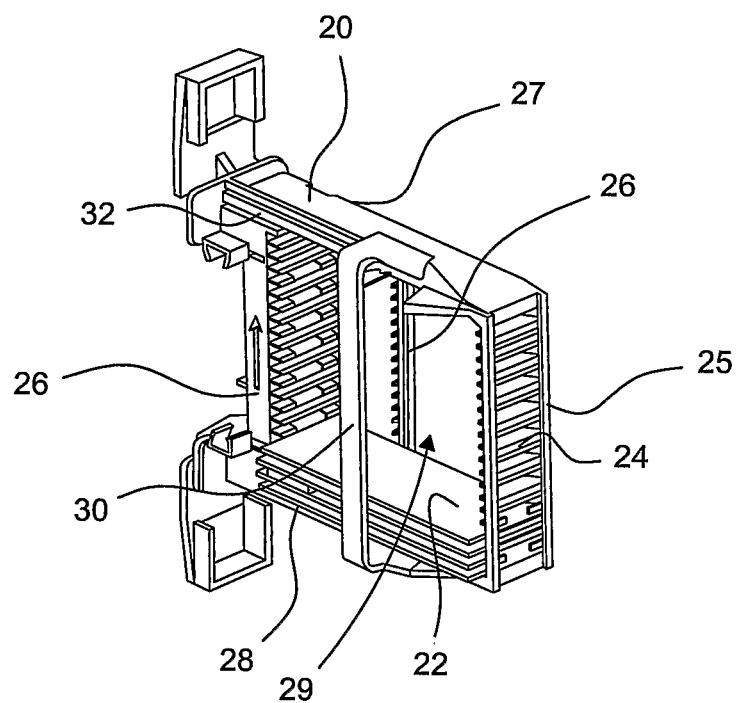
FIG. 2 shows a slide storage basket with a sliding retaining bar, being an embodiment of the present invention.

FIG. 2 shows a slide storage basket 20. The basket can hold a plurality of slides 22 and the slides can be loaded and unloaded from the side of the basket. Thus, the basket includes end support structures 24 that support the respective ends of the slides (i.e. the short sides of the rectangular slides). The end support structures 24 include ledges extending from upright members 25, such that the slides rest on the ledges. This minimises the contact between the slide and the basket, which is desirable to reduce the risk of a coverslipped slide "sticking" to the basket. This also helps to achieve easy removal of the slide from the basket after it has been coverslipped. Other areas of contact between the slide and the basket are suitably kept to a minimum, using point contact only.

The basket includes a fixed retaining member 26 that extends between the basket's top wall 27 and bottom wall 28. In this embodiment, the retaining member 26 includes a plurality of protrusions or lugs that provide further support to the underside of a slide when the slide is located in the basket.

The side of the basket opposite the fixed retaining member comprises an aperture 29 through which slides can be loaded and unloaded. The basket is therefore a side loading basket. The aperture 29 can be selectively obstructed or blocked by a slide retaining bar 30. The slide retaining bar can be moved away from the aperture during loading and unloading, and moved over the aperture during storage or transport of the basket.

The retaining bar 30 is slidably attached to the top and bottom walls of the basket. Both the top and bottom walls include a guide rail 32 along which the retaining bar can move.

The retaining bar can be moved between a retracted position (so that slides can be loaded and unloaded) and an extended position (to hold slides in the basket) by the basket processing device.

In an alternative arrangement (not shown), the retaining bar is hinged with respect to the basket.

FIGS. 3 to 8 show three slide storage basket designs. The baskets 50, 51, 52 are all of a similar type to those described in relation to FIG. 2. In other words, they are side loading baskets with a sliding retaining bar.

In addition, each of the three baskets includes two different connectors. One connector (stainer connector) is for attaching the basket to a stainer and the other connector (coverslipper connector) is for attaching the basket to a coverslipper. By providing each basket with two connectors, it is possible for the basket to be used in a stainer and in a coverslipper, thereby avoiding the need to move slides from one basket to another.

Figure 3:
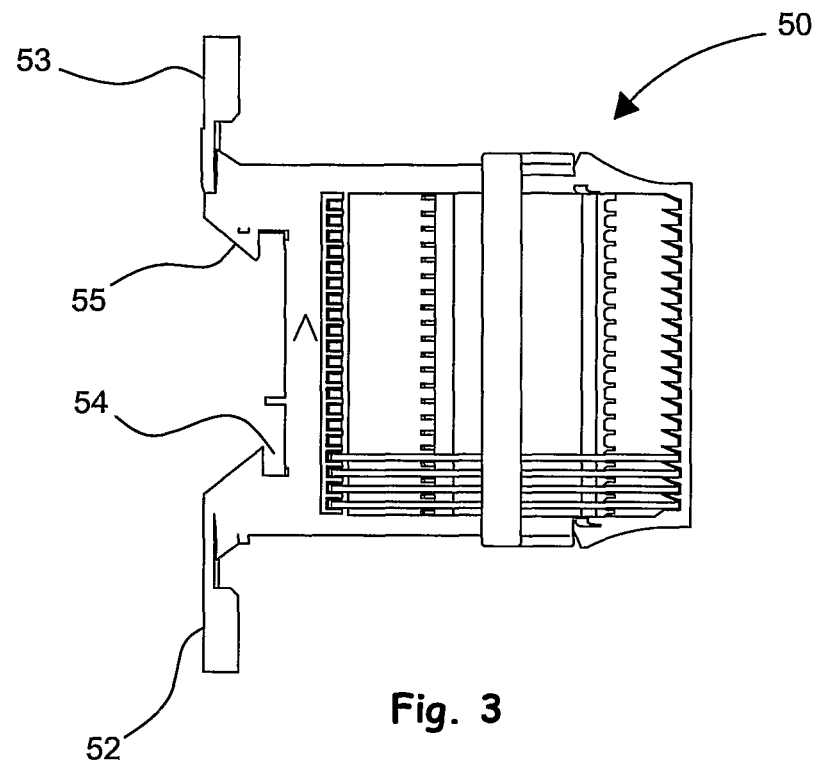
FIGS. 3 and 4 show a slide storage basket with two different connectors, being an embodiment of the present invention.
Figure 4:
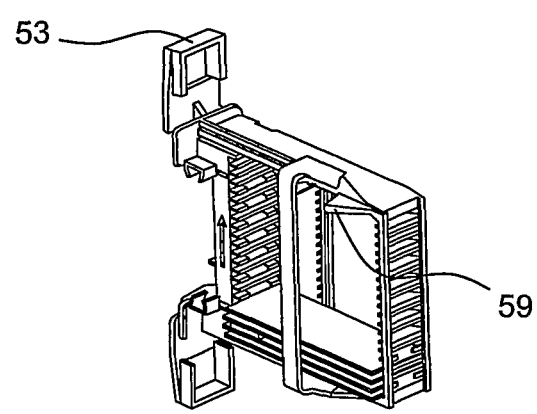
Figure 5:
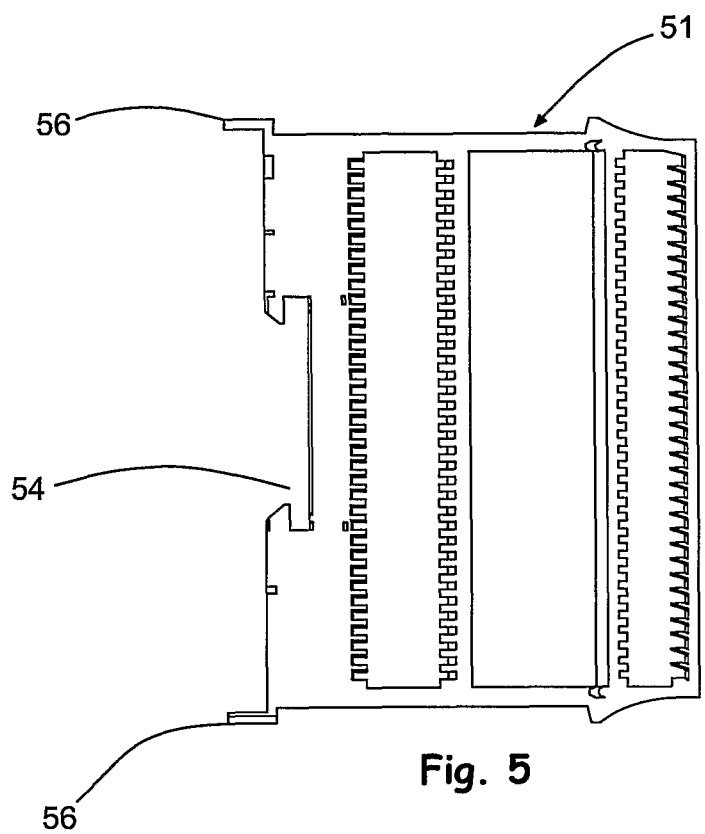
FIGS. 5 and 6 show a further slide storage basket with two different connectors, being an embodiment of the present invention.
Figure 6:
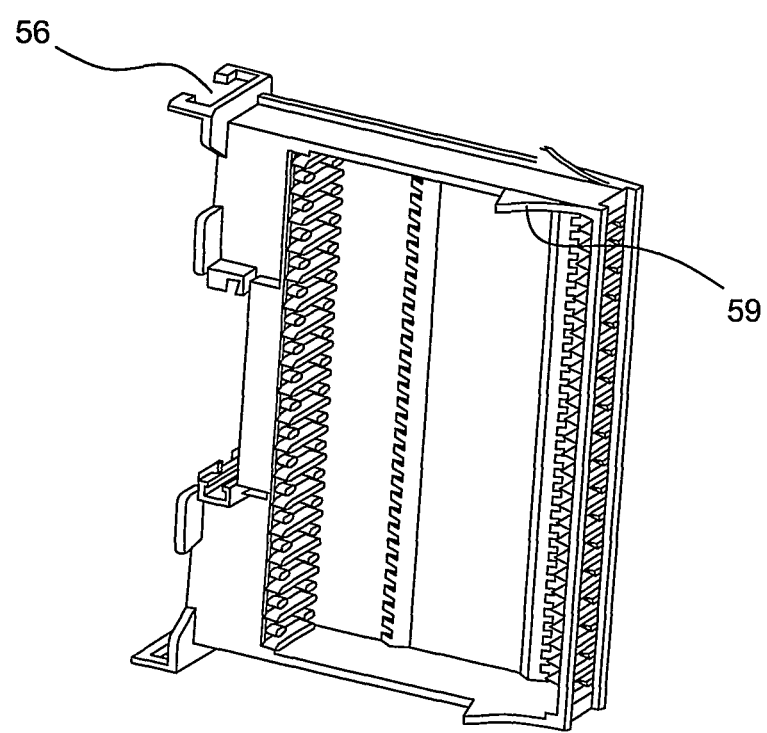
Figure 7:
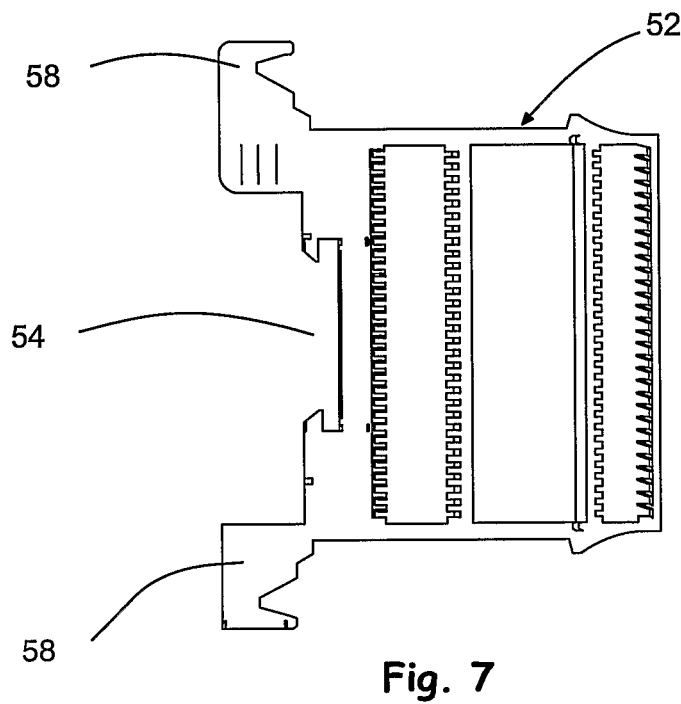
FIGS. 7 and 8 show a further slide storage basket with two different connectors, being an embodiment of the present invention.
Figure 8:
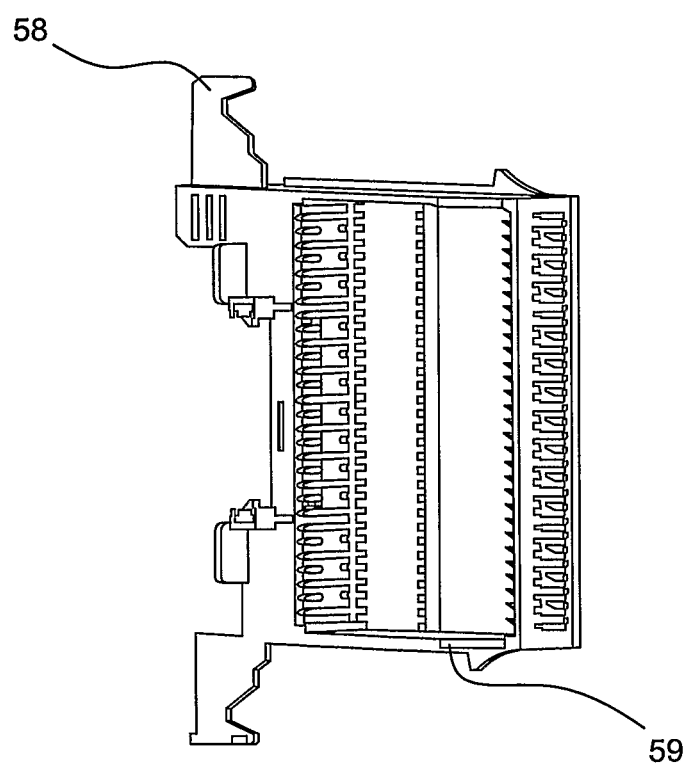

In the basket 50 shown in FIGS. 3 and 4, a pair of eye connectors 53 are provided at respective top and bottom portions on the rear of the basket. The eye connectors (sometime referred to as the "ears" of the basket) are compatible with a well known stainer and allow the basket to be attached to the basket processing mechanism of the stainer.

The basket 50 also has a load rail connector 54 that is compatible with the load rail of a coverslipper. In fact, in this embodiment, the load rail connector is adapted so that the basket can be attached to a load rail of the sort described in relation to FIG. 1.

This load rail connector 54 is common to the baskets 51 and 52 shown in FIGS. 5 to 8.

Basket 51 includes the common load rail connector as well as an additional clip connector 56. The clip connector 56 is compatible with a well known stainer and allows the basket to be attached to the basket processing mechanism of the stainer. As is clear from FIGS. 5 and 6, the clip connector 56 is provided in place of the eye connector 53. Thus, baskets 50 and 51 can be used with different stainers, but the same coverslipper.

The clip connector 56 comprises two arms extending rearwardly from the back of the basket, the distal ends of the arms comprising inturned portions to define a partially enclosed area for receiving an appropriate part of the stainer basket processing mechanism.

Turning to FIGS. 7 and 8, basket 52 again includes the common load rail connector 54 so that basket 52 can be used with the same coverslipper as baskets 50 and 51.

However, basket 52 includes a different stainer connector. Hook connector 58 is located in the same place as the eye connector of basket 50, but connector 58 allows basket 52 to be attached to the basket processing mechanism of a different stainer. Hook connector 58 includes a notch for engaging with the stainer mechanism.

In addition to the features discussed above, each of the baskets includes a spacer member, in the form of fins, which allow the sequence of basket loaded onto the coverslipper loading rail to be random, because they define the points of contact between adjacent baskets when supported next to each other on a transport rail. Thus, the space occupied by each basket on the rail is the same.

In an embodiment of one of the aspects of the present invention, a coverslipper is provided with a guard cover that is slidably attached to the coverslipper. The cover can be moved so that it prevents access to the slide processing mechanism of the coverslipper. In this way it protects the user from the hazards associated with the operation of the coverslipper. The cover can be retracted from the closed position to provide access to the slide processing mechanism, e.g. so that baskets can be added or removed.

The coverslipper includes a cover sensor that detects when the cover is in a closed position. The coverslipper also includes a slide detector that detects whether slides are waiting to be processed in the coverslipper. When the slide detector detects that slides are waiting to be coverslipped and the cover sensor detects that the cover is in a closed position, the coverslipper will start to process the slides. Thus, coverslipping can start as soon as a user closes the cover. This "autostart" arrangement avoids the need for the user to touch any buttons or switches, thereby reducing the risk of contamination and making operation easier for the user.

In another embodiment of a further aspect of the present invention, a coverslipper is provided with a cover as described above with respect to the "autostart" arrangement. In addition to the cover, the coverslipper includes an interlock that locks the cover in its closed position when the slide processing mechanism of the coverslipper is in operation. The interlock is only released when the slide processing mechanism has stopped.

In this preferred embodiment the interlock is activated by a plunger on the basket load rail of the coverslipper. The basket load rail is of the same type as the one discussed above in relation to FIG. 1. The plunger is located at one end of the load rail and is depressed by the basket pusher when the basket pusher is in its home or "parked" position. Whilst the slides/baskets are being processed, the basket pusher is located away from its home position and the plunger is no longer depressed. This results in a signal being generated, which signal causes the interlock to engage and prevents the cover from being opened. Once the coverslipper has finished processing the slides/baskets, the basket pusher of the basket load rail returns to its home or "parked" position, thereby depressing the plunger. This causes the interlock to disengage so that the cover can be moved to an open position.

Figure 9:
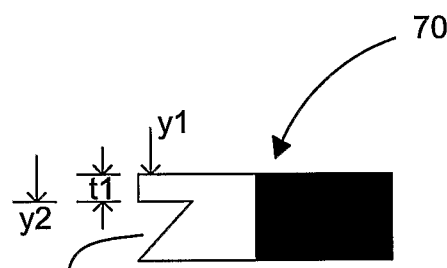
FIG. 9 shows a slide gripper of the present invention.

FIG. 9 is a schematic illustration of a slide gripper 70 that is used for holding a slide as it is moved into and out of a basket. The gripper includes a notch 72 that engages the edge of the slide. The shape of the notch is relevant to the way in which the location of the slide is detected and is discussed in more detail below.

Figure 10:
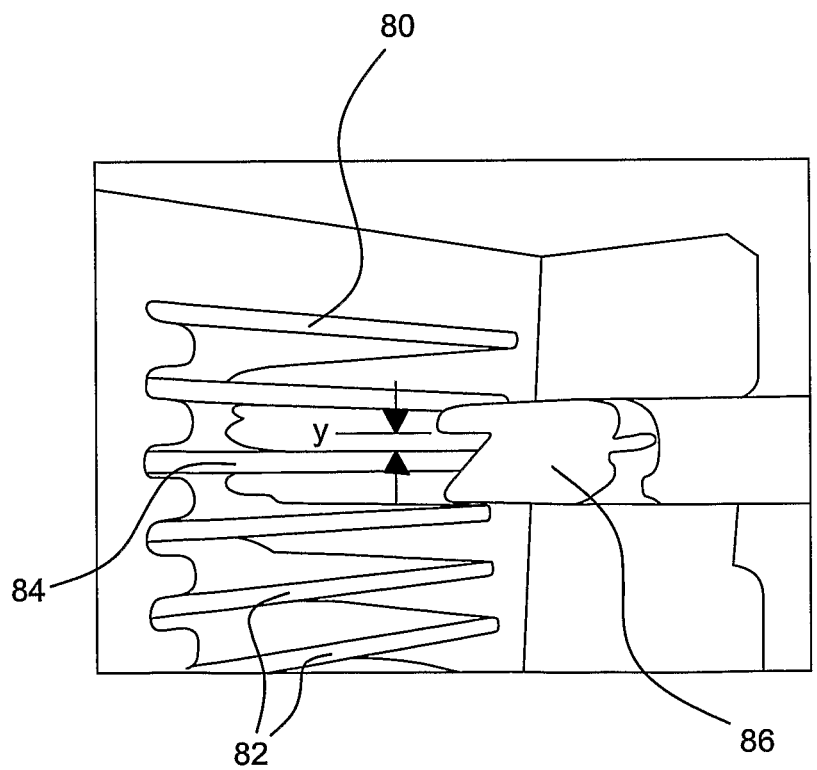
FIG. 10 shows an image of a slide generated by a slide detector of the present invention.

FIG. 10 show an image generated by a camera in a coverslipper. The camera is associated with a vertical lift system that transfers baskets from a load rail such as the one described herein.

The image is produced in greyscale, but colour images are also possible. The image shows the basket 80 and a plurality of slides 82 located in the basket. The distance between one of the slides 84 (e.g. the one to be processed next) and the slide gripper 86 is calculated by identifying the top edges of the slide and the gripper.

Indeed, a slide's position can be identified by using an edge detection algorithm and the information gained from the image can then be used to position the slide accurately between the gripper.

Firstly, using an image from the camera, the Gripper "y2" position is calculated. Once "y1" is found using an edge detection algorithm, "y2" is calculated knowing the defined thickness of the gripper "t1". The "y2" value of the gripper is used as the reference value for positioning all the slides that follow.

Once the top of the slide 84 is detected and knowing the position of the gripper "y2", the distance from the gripper to the slide "y" can be calculated. This gives a distance in Pixels which is then converted to an actual physical distance.

There can be any number of slides in a basket, from 1 to the maximum number the basket will hold. There is also the possibility that the slides are loaded non-uniformly, i.e. a gap between slides, multiple gaps or even skewed slides.

Detecting the top of the slide at multiple positions will give the slope of the slide. This value of slope can be used to detect skewed slides and therefore skip the slide to avoid damage. It is also possible to detect whether or not there is a slide in the next slots of the basket by analyzing the colour gradient below the current slide. This information can speed up the processing of the basket by moving past blank slots.

In addition the camera can be used to detect broken slides, missing/broken coverslips, skewed slides.

Figure 11:
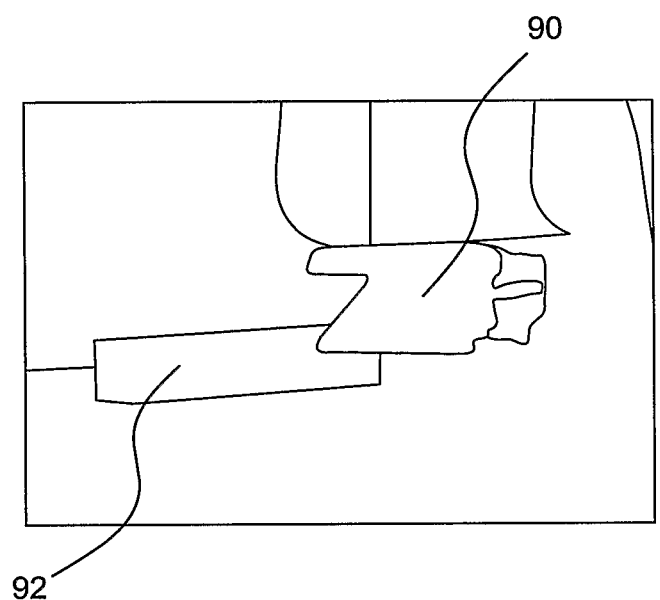
FIG. 11 shows an image of a slide storage basket generated by a basket detector of the present invention.

FIG. 11 shows another image obtained by a camera in a coverslipper. The image shows a slide gripper 90 and part of the slide retaining bar 92 of a basket. The edges and/or colour of the bar 92 are detected using known image processing technology and the operation of the coverslipper is adjusted in accordance with the type of basket detected. The user can pre-configure the coverslipper to operate in accordance with a particular protocol in response to detecting a particular basket type (e.g. particular bar colour).

For example, where two processing protocols may be needed, the present invention provides a method of identifying which protocol should be used for the basket that is to be processed next. In this embodiment, the two types of baskets are identified by having different coloured sliding retaining bars. In this embodiment, one is white and one is black.

By using a camera to detect basket features it reduces the requirement for user input, therefore making the process of coverslipping much quicker and simpler. By positioning the basket in a defined position the camera images can reveal the basket type. Thus, FIG. 11 shows an image of a basket wherein the part of the retaining bar identified in the image is "white". The slider colour is calculated by averaging a number of points within the highlighted box. 0=black, 255=white and numbers in between represent the grey scale values.

In an alternative embodiment (not shown) a colour sensor is used for a single point detection. In a further alternative embodiment (not shown) the baskets are provided with different coloured flags, for example Red or Green flags. The colour of the flags (or other coloured device) source is captured in the image and detected by appropriate image processing technology.

Figure 12:
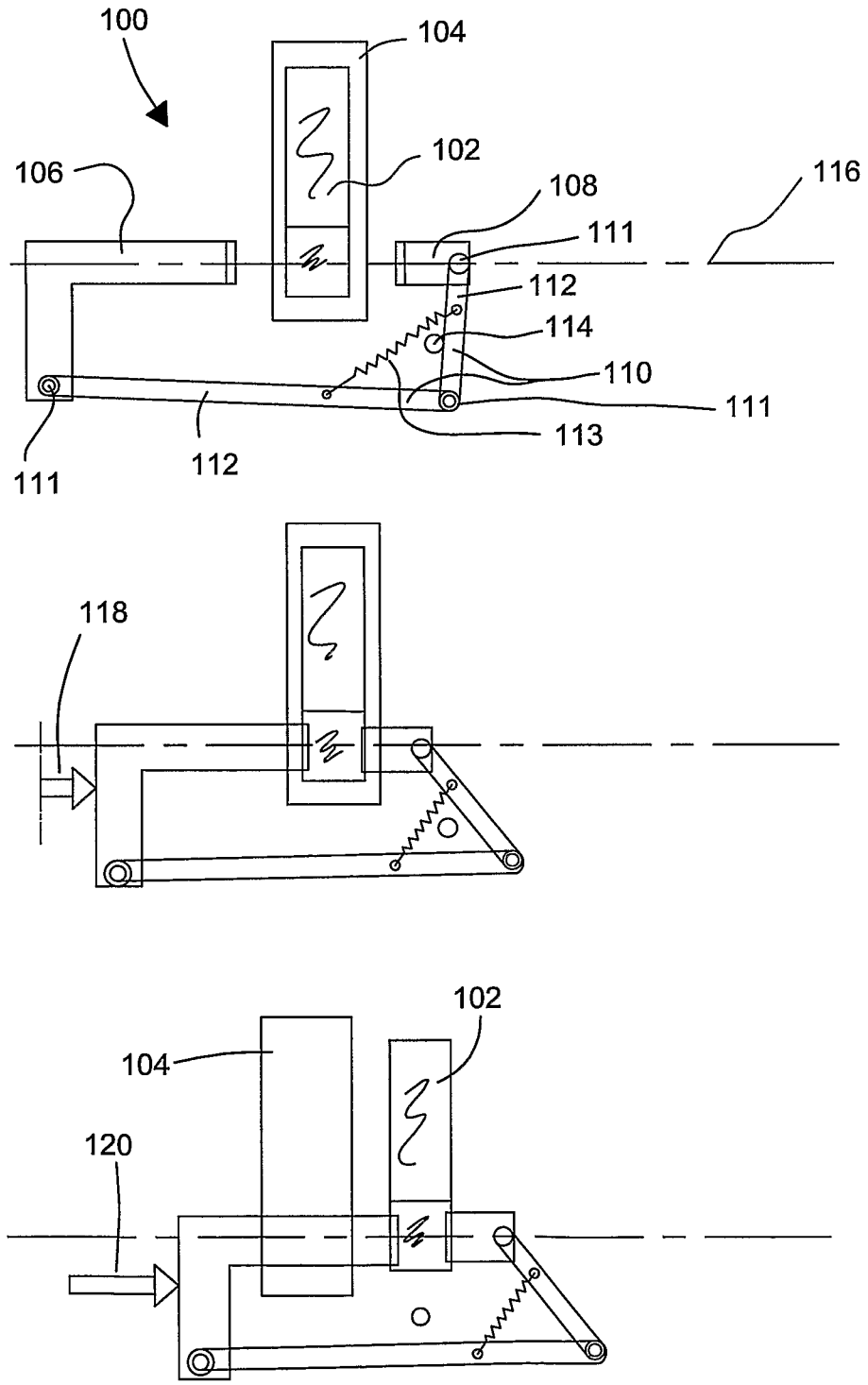
FIG. 12 shows a slide transfer device of the present invention.

FIG. 12 shows a slide transfer device comprising a slide gripper mechanism 100. The slide transfer mechanism is adapted to hold a slide 102 located in a basket 104 and to move the slide out of the basket.

The slide transfer mechanism includes two slide grippers 106, 108 that are mounted independently on linear rails so that they can both move in line, but the spacing between them can vary.

One of the slide grippers 106 is directly driven by a motor through a leadscrew (not shown). The other slide gripper 108 is connected to the directly driven gripper 106 via a linkage 110. The linkage comprises three pivoted connections 111 and two linker arms 112. The linker arms are tensioned together with a spring 113 so that the two grippers are pulled together.

The grippers are kept in the open position by fully retracting the direct driven gripper jaw. A fixed stop pin 114 causes the sprung gripper 108 to be pulled open by the linkage. The two grippers 106, 108 therefore move along a common axis 116. This is shown in the top drawing of FIG. 12.

When a slide is correctly positioned between the jaws the direct driven gripper 106 is advanced in the direction shown by arrow 118. The sprung gripper 108 will then close onto the glass slide, followed by the direct driven gripper 106. This is shown in the middle drawing of FIG. 12.

As the direct driven gripper 106 is further advanced as indicated by arrow 120, it pushes the slide out of the basket. The slide is positively held between the grippers 106, 108. This is shown in the bottom drawing of FIG. 12.

To replace the slide, the drive is reversed (i.e. the two grippers move in a direction opposite to arrows 118 and 120) and the slide is placed back into the basket. The sprung gripper 108 is disengaged from the slide after the direct driven gripper 106 has moved away from the slide, thereby ensuring that the slide is positively placed back in the basket.

The positions of the two grippers is detected by sensors (not shown). By using the gripper position information in conjunction with knowing the position of the motor it is possible to obtain an accurate measure of the width of the glass slide. In this preferred embodiment, 'flags' on the two grippers 106, 108 pass through optical sensors during use such that the gripper positions are detected. The motor associated with the direct driven gripper is a stepper motor. Feedback relating to the stepper motor position can be provided via an encoder.

Figure 13:
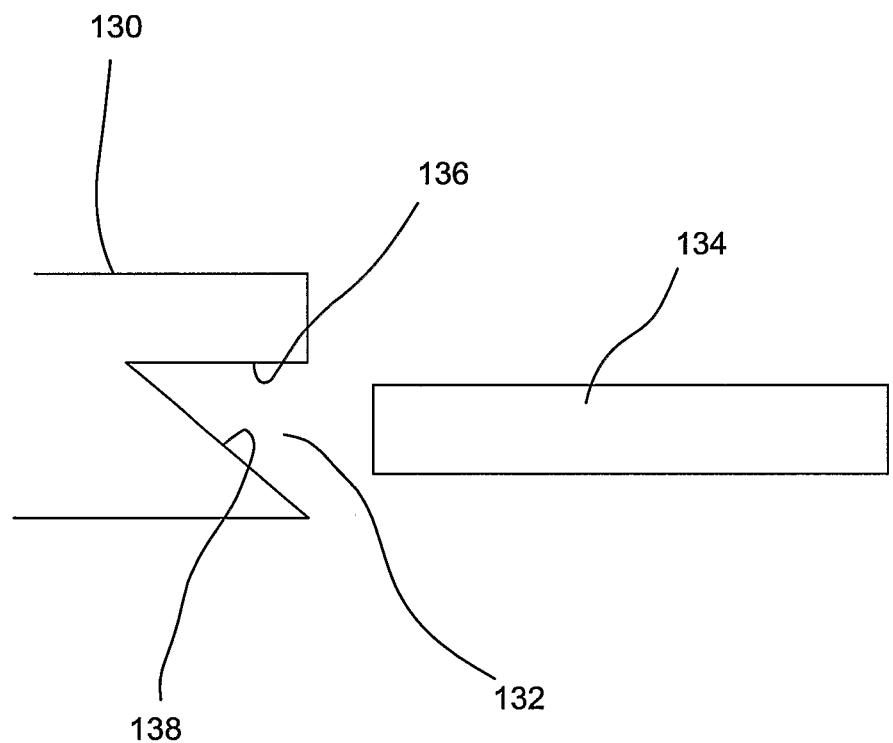
FIG. 13 shows a slide gripper of the present invention and a slide.

FIG. 13 shows the slide engaging potion of a preferred gripper 130.

The gripper has a notch 132 to enable it to grip and hold a slide 134. This notch tapers to ensure that the glass is reliably picked up and held by the gripper over a range of slide thickness variations and height tolerances within the mechanism.

The upper face 136 of the notch is horizontal while the lower face 138 is angled, at 45 degrees to the upper face. When the gripper engages the slide the upper and lower faces cause the slide to be lifted up against the upper face.

With this arrangement, the upper face is then always controlled to a known reference or datum position irrespective of the slide thickness. The datum position is also maintained for some types of slides which can have bevelled edges.

In addition the gripper system can be used in any system that requires handling of glass slides. In particular this includes slide imaging systems.

Figure 14:
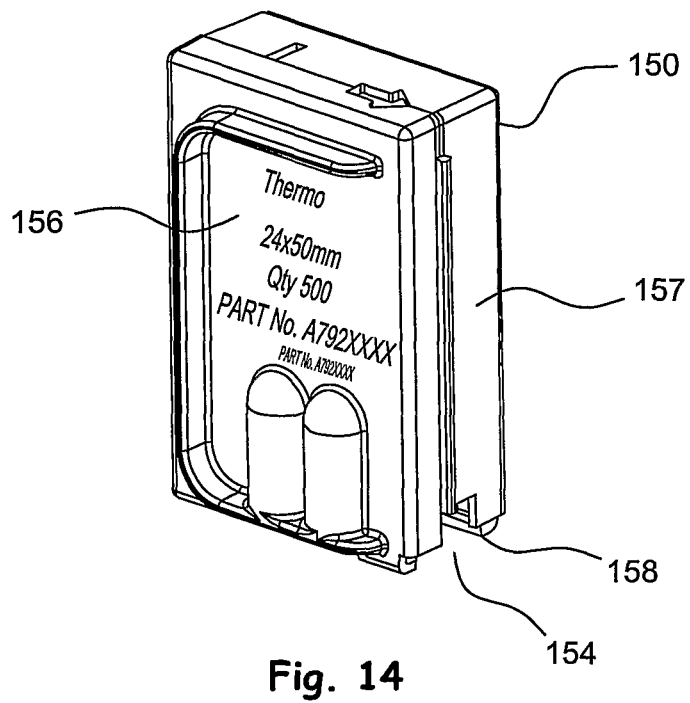
FIGS. 14 and 15 show a coverslip hopper of the present invention.
Figure 15:
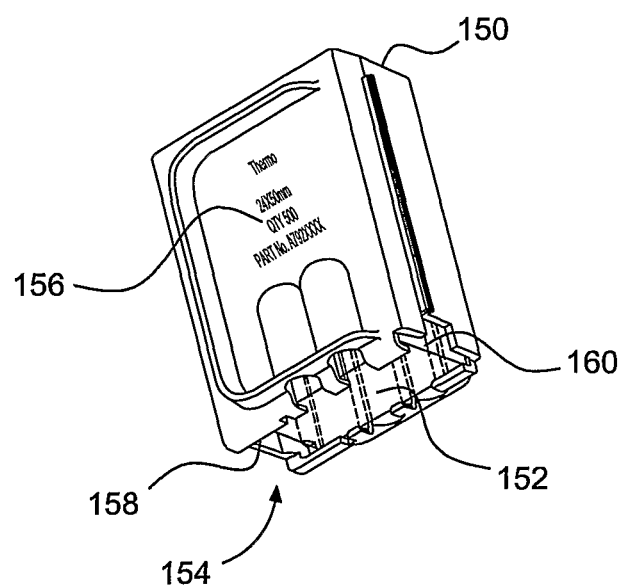
Figure 16:
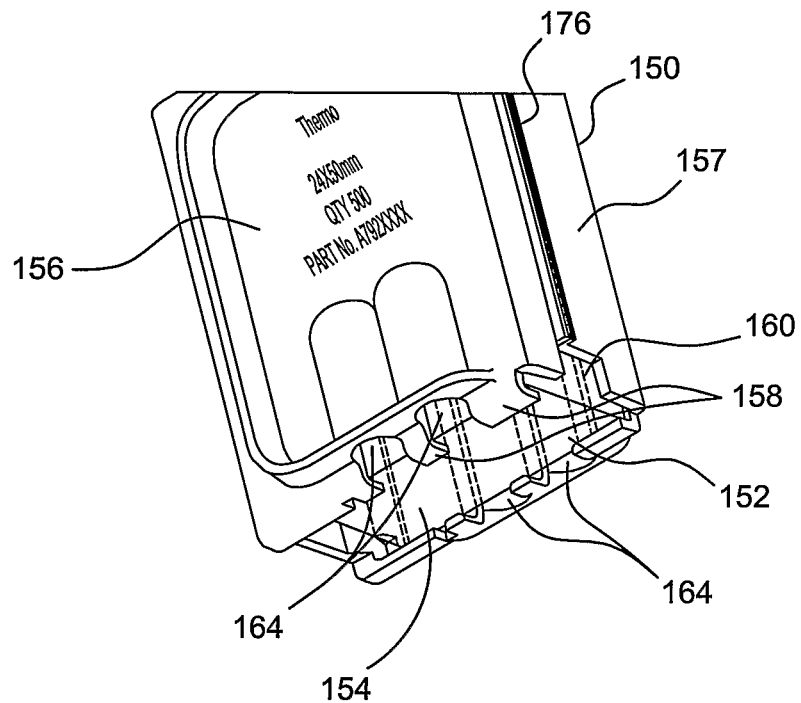
FIG. 16 shows in more detail the lower part of the hopper of FIGS. 14 and 15.

FIGS. 14 to 16 show a disposable hopper 150 according to one of the aspects of the present invention.

The design of the hopper 150 is such that it fully encapsulates a stack of coverslips 152 to provide the necessary protection to the coverslips. Only the bottom 154 of the hopper is open so that the bottommost coverslip is accessible. The hopper has sidewalls 156 and endwalls 157. Extending along the bottom edges of the sidewalls 156 of the hopper are ledges 158 which the stack of coverslips rest on to prevent them from falling out.

The front face of the hopper includes a cut away portion 160 at the bottom to allow for the bottommost coverslip to be slid out from the bottom of the stack and the rear face of the hopper has a slide stop (not shown) to prevent the bottommost coverslip being dispensed at the rear of the hopper.

Figure 17:
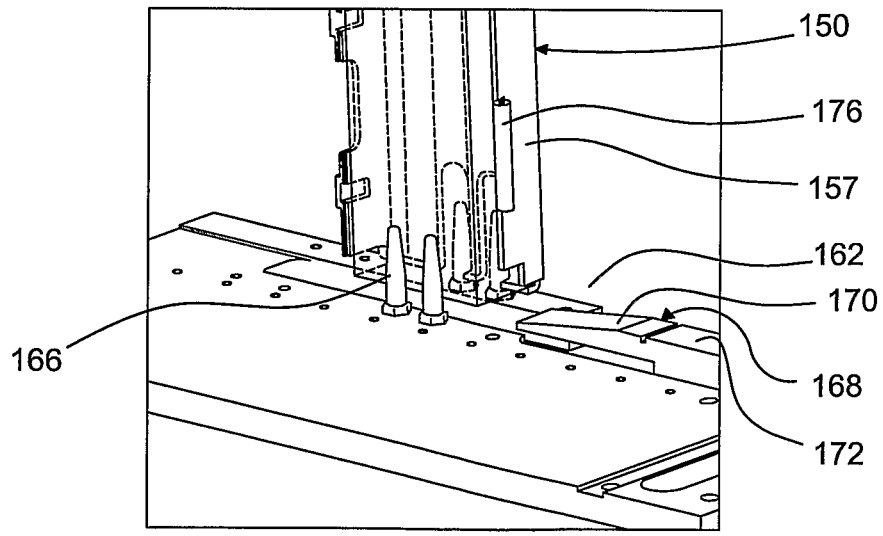
FIG. 17 shows a cut-away view of a coverslip hopper located on a coverslipper, being respective embodiments of the present invention.

As shown in FIG. 17, the hopper 150 (one half of which has been removed for clarity) is loaded into a 'docking station', being part of the coverslip dispensing mechanism 162 of the coverslipper.

The hopper 150 includes four recesses 164 formed in the sidewalls 156. Two recesses are formed in each sidewall. Each of these recesses is shaped to receive a corresponding locating pin 166 positioned on the coverslip dispensing mechanism.

The locating pins 166 have a further function and that is to tighten up the tolerance between the coverslips and the hopper. This in turn helps to provide a tighter tolerance between the coverslips and the coverslip dispensing device required for accurate and reliable coverslip dispensing. This is achieved by forming the recesses 164 so that when the locating pins 166 are inserted into the recesses, they intrude into the internal space of the hopper. The locating pins therefore push against the sides of the coverslips and guide them into the desired alignment.

The recesses 164 and locating pins 166 ensure that the hopper is correctly positioned on the coverslip dispensing mechanism and in the correct orientation.

Figure 18:
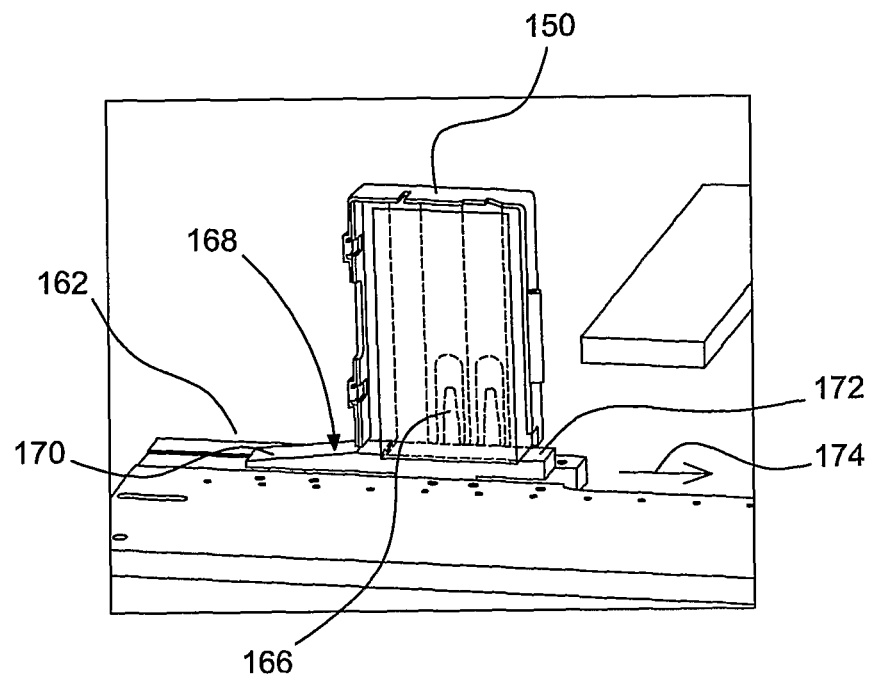
FIG. 18 shows a further cut-away view of the hopper and coverslipper of FIG. 17.

Once the hopper 150 has been loaded onto the coverslip dispensing mechanism, the coverslip stack 152 within the hopper is lifted off the ledges on the hopper onto a dispensing carriage 168. The dispensing carriage has a tapered or wedge-shaped rear portion 170. The carriage moves from the front of the hopper to the back of the hopper. The increasing thickness of the tapered rear portion causes the coverslips to lift away from the ledges 158 on the bottom of the hopper. The carriage 168 includes a machined step that that separates the tapered rear portion and a planar front portion 172. When the tapered portion has moved past the coverslips, the coverslips are supported on the planar front portion 172. This is shown in FIG. 18.

From this position, the carriage 168 then moves in a forward direction as indicated by arrow 174, i.e. so that the tapered rear portion is moved towards the front of the hopper 150. This forward movement causes the bottommost coverslip to be engaged by the machined step on the carriage. The bottommost coverslip is therefore retained on the planar front portion 172 as the carriage moves towards the front of the hopper. This action therefore dispenses a coverslip. As the carriage 168 passes from underneath the hopper the weight of the stack of coverslips 152 is once more taken up by the ledges 158 in the hopper.

As the carriage 168 retracts back under the coverslip stack (i.e. moves towards the rear of the hopper), the stack is lifted back onto the carriage by means of the tapered profile of the carriage. The carriage retracts far enough back to allow the machined step to pick up the next coverslip.

Once the hopper 150 is empty or there is problem, the hopper can be removed and a new one loaded in its place.

Figure 19:
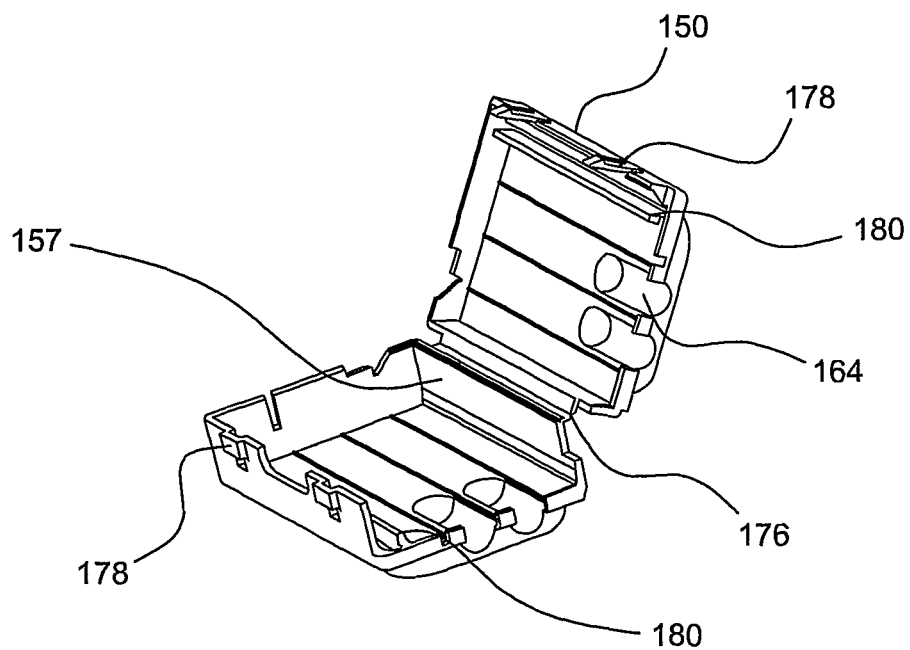
FIG. 19 shows a hinged hopper, being an embodiment of the present invention.

FIG. 19 shows the disposable hopper 150 in an open configuration. The hopper 150 includes a hinge 176 that allows the hopper to open with a "clam shell" action. This provides convenient access to the interior of the hopper and makes loading of the hopper easier. The hinge is formed in one of the endwalls 157 to provide a large opening through which coverslips can be loaded.

The hopper 150 includes a latch 178 comprises cooperating resilient members located on respective halves of the hinged hopper. This allows the hopper to be closed securely after loading with coverslips. In some embodiments, the design of the latch mechanism is adapted so that the hopper can be re-used, whereas in other embodiments, the latch can be adapted so that it can only be used once, after which it is thrown away.

As shown in FIG. 19, internal ribs 180 are molded into the inner walls of the hopper to allow for different length coverslips to be loaded whilst keeping the outside of the hopper unchanged.

As shown in FIGS. 14 to 16, the hopper also includes external rib 182. This provides a convenient aid to handling the hopper and also imparts structural integrity to the hopper.

The hopper is manufactured from a plastics material as a one piece molding, including the hinge, latch and ribs.

These preferred embodiments have been described by way of example and it will be apparent to those skilled in the art that many alterations can be made that are still within the scope of the invention.

The invention claimed is:

1. A hopper for storing a plurality of coverslips prior to dispensing of said coverslips by a coverslip dispensing device, wherein the hopper is configured to cooperate with the coverslip dispensing device so as to align the hopper with respect to the coverslip dispensing device,
    wherein the hopper comprises opposing walls partially defining an interior space for holding a stack of coverslips,
    wherein a plurality of recesses are formed within the opposed walls, the plurality of recesses being adapted to allow elongated members of the coverslip dispensing device to intrude into the interior space and engage the side of the stack of coverslips such that a plurality of coverslips are simultaneously engaged by the elongated members,
    wherein the plurality of recesses comprises a plurality of elongated concave surfaces formed within and extending vertically up the opposing walls.

2. A hopper according to claim 1, wherein at least one recess is tapered.

3. A hopper according to claim 1, wherein the hopper has front and back walls that are adjacent to the opposing sidewalls.

4. A hopper according to claim 1, wherein the hopper is made from a plastics material.

5. A hopper according to claim 4, wherein the hopper is made from a one-piece molding.

6. A hopper according to claim 4, wherein the hopper is disposable.

7. A hopper according to claim 1, wherein the hopper includes an opening through which coverslips can be loaded into the hopper.

8. A hopper according to claim 7, wherein the hopper includes front and rear end walls joining the opposed walls, wherein one of the hopper walls that is moveable with respect to the other walls so as to selectively provide the opening through which coverslips can be loaded into the hopper.

9. A hopper according to claim 8, wherein the at least one hopper wall is hinged with respect to the other walls so as to provide a hinged opening for loading the hopper.

10. A hopper according to claim 8, wherein the hopper includes a latch so that the at least one hopper wall can be selectively held in a closed position.

11. A hopper according to claim 1, wherein the hopper includes internal guides for locating coverslips within the hopper.

12. A hopper according to claim 11, wherein the hopper includes a plurality of walls defining the internal volume of the hopper, and the internal guides define a space within the hopper that is smaller than the internal volume of the hopper to permit a coverslip smaller than the hopper to be stored in the hopper.

13. A hopper according to claim 11, wherein the internal guides are arranged to reduce the effective length of the hopper.

14. A hopper according to claim 11, wherein the internal guides comprises one or more ribs.

15. A hopper according to claim 14, wherein the ribs extend substantially from the bottom of the hopper to the top of the hopper.

16. A hopper for storing a plurality of coverslips prior to dispensing of said coverslips by a coverslip dispensing device, wherein said hopper includes an opening that selectively provides an opening through which coverslips can be loaded into the hopper,
    wherein the hopper comprises opposing walls partially defining an interior space for holding a stack of coverslips,
    wherein the hopper comprises a plurality of recesses within the opposed walls, the plurality of recesses having elongated concave surfaces and being adapted to allow elongated members of the coverslip dispensing device to intrude into the interior space and engage the side of the stack of coverslips such that a plurality of coverslips are simultaneously engaged by the elongated locating pins.

17. A hopper for storing a plurality of coverslips prior to dispensing of said coverslips by a coverslip dispensing device, wherein said hopper includes internal guides for locating coverslips within the hopper,
    wherein the hopper comprises opposing walls partially defining an interior space for holding a stack of coverslips,
    wherein the internal guides comprise a plurality of recesses within the opposed walls, the plurality of recesses having elongated concave surfaces and being adapted to allow elongated members of the coverslip dispensing device to intrude into the interior space and engage the side of the stack of coverslips such that a plurality of coverslips are simultaneously engaged by the elongated locating pins.

18. A coverslip dispensing device configured for cooperating with a hopper so as to align the hopper with respect to a coverslipper,
    wherein the hopper comprises opposing walls partially defining an interior space for holding a stack of coverslips,
    wherein the coverslip dispensing device comprises a plurality of elongated locating pins and the opposing walls comprise a plurality of recesses within the opposed walls, the plurality of recesses having elongated concave surfaces and being adapted to allow the elongated locating pins of the coverslip dispensing device to intrude into the interior space and engage the side of the stack of coverslips such that a plurality of coverslips are simultaneously engaged by the elongated locating pins.

19. A coverslip dispensing device according to claim 18, wherein two locating pins of the plurality of locating pins are provided side by side.

20. A coverslip dispensing device according to claim 18, wherein at least one locating pin is tapered.

21. A hopper for storing a plurality of coverslips prior to dispensing of said coverslips by a coverslip dispensing device, the hopper having front and back walls and a pair of opposing sidewalls, wherein at least one of the hopper walls is moveable with respect to the other walls so as to selectively provide an opening through which coverslips can be loaded into the hopper, and the hopper having a latch so that the at least one wall can be selectively held in the closed position, and the hopper being configured for cooperating with the coverslip dispensing device so as to align the hopper with respect to the coverslip dispensing device, wherein the opposing sidewalls partially define an interior space for holding a stack of coverslips, wherein the opposing sidewalls comprise a plurality of recesses within the opposed walls, the plurality of recesses having elongated concave surfaces and being adapted to allow elongated locating pins of the coverslip dispensing device to intrude into the interior space and engage the side of the stack of coverslips such that a plurality of coverslips are simultaneously engaged by the elongated locating pins.

22. A hopper according to claim 21, wherein the moveable at least one hopper wall is hinged with respect to the other walls so as to provide a hinged opening for loading the hopper.

23. A hopper for storing a plurality of coverslips prior to dispensing of said coverslips by a coverslip dispensing device, wherein the hopper includes elongated locating chambers for cooperating with the coverslip dispensing device so as to align the hopper with respect to the coverslip dispensing device, wherein the elongated locating chambers are adapted so that aligning the hopper with elongated locating pins of the coverslip dispensing device causes a stack of coverslips inside the hopper to be aligned within the hopper, wherein the opposing sidewalls partially define an interior space for holding the stack of coverslips, wherein the elongated locating chambers comprise a plurality of recesses within the opposed walls, the plurality of recesses having elongated concave surfaces and being adapted to allow the elongated members of the coverslip dispensing device to intrude into the interior space and engage the side of the stack of coverslips and thereby causes the stack of coverslips inside the hopper to be aligned within the hopper such that a plurality of coverslips are simultaneously engaged by the elongated locating pins.

* * * * *